United States Patent [19]
Horwege et al.

[11] Patent Number: 5,881,386
[45] Date of Patent: Mar. 16, 1999

[54] FLEXIBLE POLYVINYL CHLORIDE ARTICLE AND METHOD OF MAKING

[75] Inventors: Kenneth S. Horwege, Boulder Creek; Donna L. Reuck, San Jose; Mark E. Vande Pol, Los Gatos, all of Calif.

[73] Assignee: Maxxim Medical, Inc., Clearwater, Fla.

[21] Appl. No.: 172,453

[22] Filed: Dec. 23, 1993

[51] Int. Cl.[6] .............................. A41D 19/00; B32B 5/16; B32B 27/40
[52] U.S. Cl. ................................ 2/161.7; 2/167; 428/220; 428/325; 428/327; 428/331; 428/423.1; 428/424.6; 604/292
[58] Field of Search .......................... 2/159, 161.7, 161.8, 2/167, 168; 428/219, 220, 323, 325, 327, 331, 423.1, 424.6; 604/292

[56] References Cited

U.S. PATENT DOCUMENTS

| | | | |
|---|---|---|---|
| 3,059,241 | 10/1962 | O'Brien et al. | 2/167 |
| 4,143,109 | 3/1979 | Stockum | 264/112 |
| 4,947,487 | 8/1990 | Saffer et al. | 2/161.7 |
| 5,088,125 | 2/1992 | Ansell et al. | 2/167 |

*Primary Examiner*—D. S. Nakarani

[57] ABSTRACT

A two layer flexible article includes a first layer of polyvinyl chloride (PVC) and a second layer of polyester polyurethane which incorporates a texturizing agent. The article preferably is a glove formed by the method of dipping a hand shaped form into a first bath containing a PVC plastisol and a second bath containing a polyester polyurethane emulsion incorporating a texturizing agent and a slip agent. In a finished glove of the present invention the PVC layer forms the outside or patient contacting surface and the polyester polyurethane with the texturizing agent and the slip agent incorporated therein forms the inner user contacting surface. Gloves of the present invention are substantially donnable without the need for donning powders.

8 Claims, 3 Drawing Sheets

FLEXIBLE POLYVINYL CHLORIDE ARTICLE AND METHOD OF MAKING

FIELD OF THE INVENTION

This invention relates to flexible articles and more particularly to powder-free examination gloves formed from polyvinyl chloride and a method of making same.

BACKGROUND OF THE INVENTION

Flexible waterproof gloves are important tools for the medical profession. Traditionally these gloves were formed from natural rubber latex by dipping hand shaped forms into the latex, curing the latex into a continuous film and them removing the glove from the form. Since gloves formed from natural rubber are inherently self-adherent, it was necessary to apply powder release agents on the forms prior to dipping so that the formed glove would not adhere to the forms.

Natural rubber latex is expensive and may present allergy potential. With the development of synthetic polymers it has become possible to produce flexible film gloves from materials other than natural rubber latex. Polyurethanes and acrylates can be formed into latices similar to natural rubber and polyvinyl chloride (PVC) can be prepared as a plastisol so that film gloves with substantially similar properties to natural rubber latex gloves may be prepared. Representative of these vinyl gloves are Tru-Touch® sold by Becton Dickinson, Franklin Lakes, N.J.

Gloves prepared from PVC plastisol are also self-adherent and powdered release agents similar to those used in latex gloves are used for these PVC gloves.

With the advent of Human Immunodeficiency Virus (HIV), film gloves are being worn more often and more frequently by laboratory workers and physicians. Many workers who previously wore gloves only occasionally are now required to wear gloves almost continually. This increased usage has resulted in much greater exposure of the user populations to the gloves and instances of allergic sensitivity to some of the materials used in forming gloves and to the release powders used in gloves have been reported. Additionally, for some applications, the presence of release powder on a glove may interfere with the procedure which the user is conducting while wearing the glove. There are several reports related to elimination of release powders on natural rubber glove such as utilizing chemical treatments such as halogenation of the natural rubber surface and bonding lubricious agents to the surface of the glove.

U.S. Pat. No. 5,088,125 to Ansell et al. teaches an elastomeric glove wherein good donning characteristics are obtained without the need for donning agents such as talc and without the need to produce an inner laminate by polymerization methods. The patent further teaches that a glove may be formulated from a first flexible elastomeric material having a hand contacting surface of the glove coated with a second elastomeric material comprising a blend of an ionic polyurethane and a dispersed second polymer having a particle size greater than that of the ionic polyurethane. Only organic polymeric materials having a particle size greater than the polyurethane are suggested for the dispersed particulate materials.

U.S. Pat. No. 4,143,109 to Stockum teaches a method of making a medical glove adapted to tightly uniform to a wearer's skin and to be donned without the use of additional lubricants. The patent teaches medical glove having an outer layer of elastomeric material. A separate inner layer of elastomeric material bonded to the outer layer and particulate matter securely embedded in and randomly distributed throughout the inner layer. The particulate matter is preferably partially exposed on the inner skin contacting layer so that it extends beyond the inner surface to form protrusion on the inner surface in a size and shape and in a quantity distribution similar to a powdered glove. The patent teaches the use of polyethylene microbeads as well as other polymers, both naturally occurring and man made. Cornstarch and cross-linked corn starch are taught as particularly suitable materials and as having desirable lubricity properties.

While the teachings of the above referenced patents provide one skilled in the art of making gloves with several ways of providing gloves which are donnable without the need for release powders, there is still a need for a vinyl glove with which is donnable without powder which does not depend solely on lubricious properties of a partially exposed embedded material and which can be produced efficiently.

SUMMARY OF THE INVENTION

A flexible article includes a first layer comprising plasticized polyvinyl chloride resin and a second layer adhered to the first layer. The second layer includes a polyester polyurethane, a slip agent and a texturizing agent.

The article preferably may be a two layer glove useful in medical procedures. The glove includes a first patient contacting layer formed as a film from a plasticized polyvinyl chloride resin and a second user contacting layer formed as a film from a polyester polyurethane. The patient contacting layer is preferably formed from a fused polyvinyl chloride gel plasticized with a plasticizer such as phthalate esters, adipate esters and the like.

The user contacting layer preferably includes a slip agent and a texturizing agent providing the surface with a texture so that the user contacting layer will slide on itself and on the user's skin thus rendering the glove of the present invention donnable without the need for powder.

A method forming gloves of the present invention useful in medical procedures includes dipping a clean hand mold having a surface into a first bath containing a polyvinyl chloride plastisol. A plastisol film is formed on the mold surface, then the mold is removed from the first bath. The mold with the first film on its surface is heated to cause the plastisol to gel and fuse. The mold with the first film on its surface is then cooled and dipped into a second bath which includes an aqueous suspension of a polyester polyurethane, a slip agent and a texturizing agent. A second film of polyester polyurethane, slip agent and texturizing agent is then formed over the first film and the mold having the first film and second film is removed from the second bath. The mold having the first film and second film on its surface is then heated drying and adhering the first film and second film. This forms a two layer unitary structure on the surface of the mold. A cuff is then formed on the unitary structure on the mold. The unitary structure is then stripped from the mold surface by everting, forming a glove having a patient contacting layer on an outside surface and a user contacting layer on an inside surface.

A process for making a glove useful in medical procedures includes forming a first layer from a polyvinyl chloride plastisol on an outside surface of a hand shaped mold. A second layer of polyester polyurethane, a slip agent and a texturizing agent is then formed over and adherent to the first layer on the mold.

Gloves of the present invention are highly flexible, have excellent elongation and strength properties while having a thickness which allows excellent tactile sensitivity. Additionally, the presence of the slip agent and the texturization agent in the user contacting layer facilitate the stripping and everting of the gloves from the mold allowing efficiencies of manufacture not previously possible in a powder-free glove. The slip agent and the texturizing agent render the glove substantially not self-adherent and facilitate donning of the glove by the user without the need for powder on the surface.

DETAILED DESCRIPTION

Figure 1:
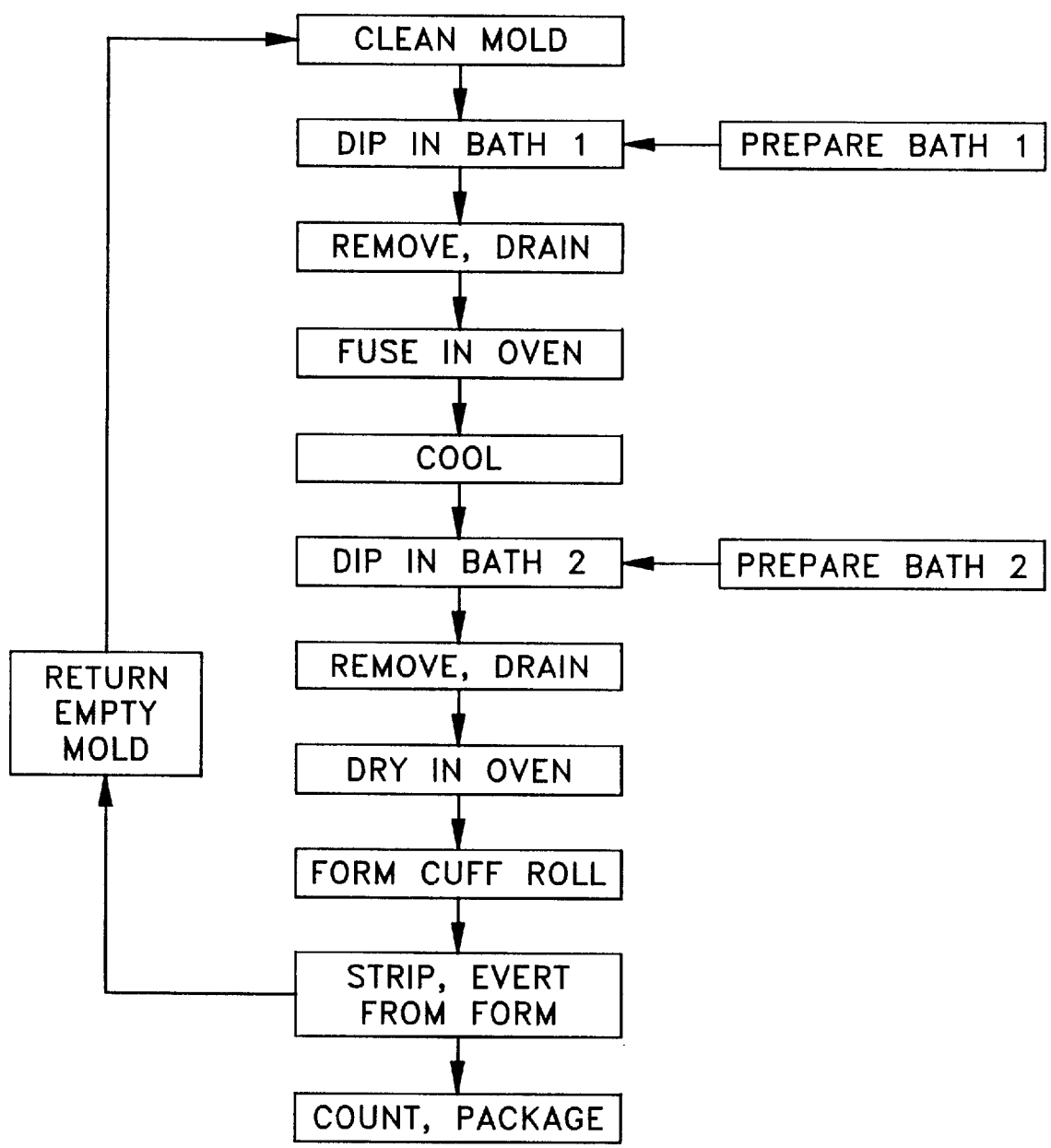
FIG. 1 shows a schematic of a process for forming powder free gloves of the present invention.

While this invention is satisfied by embodiments in many different forms, there will be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the present invention, a flexible article can be prepared which has a first layer formed from plasticized polyvinyl chloride (PVC) or a PVC copolymer and a second layer, adhered to the first layer, of polyester polyurethane, a slip agent and a texturizing agent.

A glove useful in medical procedures includes a first patient contacting layer formed as a film from plasticized polyvinyl chloride (PVC) or PVC copolymers and a second layer, adherent to the first layer, for contacting the user formed from a polyester polyurethane. The glove of the present invention preferably includes a slip agent and a texturizing agent in the user contacting layer. The presence of the slip agent and the texturizing agent allow the user contacting layer to slide against itself and provide the surface of the user contacting layer with a micro-roughness substantially reducing the contact area between the user's skin and the glove surface, thereby allowing the glove to be donned without the powder required by current PVC gloves.

In powdered gloves, the powder functions as a lubricant by separating the glove surfaces and preventing self adherence as well as allowing the glove surface to slide against the user's skin by reducing the contact area. U.S. Pat. No. 4,143,109 to Stockum teaches that an elastomeric glove substrate may have a second layer over the substrate layer having a particulate suspension in an elastomeric material. Stockum teaches that the particulate should have a size greater than the thickness of the second layer so that the particulate will protrude through the surface, having exposed portions extending outwardly so that the lubricity properties of the particulate are available for making the surface slippery. The patent further teaches that the particles preferably are physiologically inert, smooth surfaced and have a low coefficient of friction. The preferred material taught by Stockum is an epichlorohydrin cross-linked corn starch, a material used in many powdered gloves as a lubricant powder.

Surprisingly, the present invention is able to utilize materials commercially used as abrasives such as calcium carbonate, synthetic amorphous silicates, silicates, diatomaceous earth and glass beads. In the present invention, the finely divided material used as a texturizing agent in the user contacting layer is substantially coated by the polyester polyurethane, providing a slip enhancing surface not by being partially exposed and hence potentially dislodgeable, but rather by preventing the surface from being substantially smooth, thus substantially reducing contact between the glove surface and the user's skin thereby reducing friction.

Samples from several commercially available powder free gloves were tested against the present invention for peak static coefficient of friction (COF) using ASTM Test Method D-1894, hereby incorporated by reference. The test apparatus (Kayeness D5095D) was set at 15.2 cm/minute with 190 grams on the sled. Table I gives the coefficient of friction and the standard deviation (inside parenthesis) at ambient temperature (between about 23° C. to about 30° C. ) and at elevated temperature (between about 65° to about 77° C.). For the purposes of this experiment the temperature deviations within the ambient and within the elevated range were not significant.

TABLE I

Ambient and Elevated Temperature Coefficient of Friction with (Standard Deviation)

| Sample | Temp. | |
|---|---|---|
| | 23–30° C. | 65–77° C. |
| Present Invention | 0.21 (.06) | 0.35 (0.05) |
| Allerderm Powder Free ™ Allerderm Laboratories | 0.33 (0.04) | 1.08 (0.19) |
| Alpine Powder-Free ™ Alpine Products | 0.6 (0.08) | 1.43 (0.12) |
| Oak Powder Free ™ Oak Rubber Corp. | 0.37 (0.02) | 1.39 (0.39) |

The results show that the present invention has a lower coefficient of friction than the other commercially available products tested. Additionally, the presence of the oxidized polyethylene slip agent in the second layer of the present invention is believed to provide the substantially lower coefficient of friction at the elevated temperature. This lower coefficient of friction at elevated temperatures facilitates rapid stripping and everting of gloves of the present invention from the molds.

Given below is a list of materials found to be suitable for use in the representative example of the preferred embodiment of the present invention. These reagents and the following examples are intended to be exemplary but not limitative of the present invention, the method and the process for forming the present invention in its preferred embodiment, a glove suitable for use in medical procedures.

| Trade Name | Source |
|---|---|
| I. Polyvinyl chloride (PVC) or PVC copolymer Dispersion Resin Intrinsic Viscosity (ASTM D-1243 Method A) between about 0.7 to about 1.5. | |
| a) Geon 121X10 | GEON, Inc. Cleveland, OH |
| b) Oxy 80HC | Oxychemical Dallas, TX |
| c) NV2 Formalon | Formosa Chemical Livingston, NJ |
| d) KV2 Formalon | Formosa Chemical Livingston, NJ |

-continued

| Trade Name | Source |
| --- | --- |
| e) FPC 6337 | Oxychemical Dallas, TX |
| f) Pliovic DR-600, 602, 652 | Goodyear Chemicals Akron, OH |
| g) Pliovic MC-85 copolymer | Goodyear Chemicals Akron, OH |
| h) VC 1070, VC 1071 | Borden Chemical Geismar, LA |
| i) EH-71 | Georgia Gulf Plaquemine, LA |
| II. Plasticizer for PVC | |
| Phthalate based | |
| a) Santicizer 711 | Monsanto St. Louis, MO |
| b) Jayflex DOP | Exxon, Houston, TX |
| c) Jayflex 77 | Exxon, Houston, TX |
| d) Jayflex DINP | Exxon, Houston, TX |
| e) Kodaflex DOTP | Eastman, Kingsport, TN |
| Adipate based | |
| a) Kodaflex DOA | Eastman, Kingsport, TN |
| b) Jayflex DINA | Exxon, Houston, TX |
| III. Stabilizer | |
| Suitable stabilizers include epoxidized tall oil, epoxidized soybean oil, transition metal soaps and the like. | |
| a) Drapex 4.4 | Witco, NY, NY |
| b) Drapex 6.8 | Witco, NY, NY |
| c) Interstab CZL-717 | Akzo, Dobbs Ferry, NY |
| c) Interstab LT-4468 | Akzo, Dobbs Ferry, NY |
| IV. Viscosity Modifiers | |
| a) Jayflex 215 (paraffin oil) | Exxon, Houston, TX |
| b) Deplastol (polyether glycol) | Henkel, Ambler, PA |
| c) Keltrol RD (xanthan gum) | Kelco, San Diego, CA |
| d) Kelzan (xanthan gum) | Kelco, San Diego, CA |
| V. Texturizing Agents | |
| a) Atomite (calcium carbonate) | ECC America Sylacauga, AL |
| b) Duramite (calcium carbonate) | ECC America Sylacauga, AL |
| c) Celite (diatomaceous earth) | Hill Bros. Chem. Orange, CA. |
| d) Zeothix, Zeolite (aluminosilicates) | J. M. Huber Havre de Grace, MI |
| e) Sipernate (silicate) | Degussa Ridgefield Park, NJ |
| V. Slip Agent (Oxidized Polyethylene Emulsion) | |
| a) Polyemulsion OA3N30 | Chemical Corp. of Amer. E. Rutherford, NJ |
| b) Polyethylene OA3 | Michelman, Inc. Cincinnati, OH |
| VI. Flow Enhancer (Microcrystalline Cellulose) | |
| a) Lattice NT020 | FMC, Phila. PA |
| b) Avacel PH105 | FMC, Phila. PA |
| VII. Polyester Polyurethane Emulsion | |
| a) Solucote 10511-3-35 | Soluol Chem. Co. West Warwick, RI |
| b) Impranil DLN | Miles, Inc. El Toro, CA |
| VIII. Antifoam Agent (Alkoxylate Fatty Acid) | |
| Bubble Breaker 625 | Witco, Houston, TX |
| IX. Surface Active Agent (Modified Aliphatic Polyether) | |
| a) Antarox LF330 | Rhone Poulenc Cranbury, NJ |
| b) BYK-345 | BYK Inc., Wallingford, CT |

EXAMPLE

Referring to the process schematic (FIG. 1) for preparing a preferred embodiment of the present invention, a clean mold having the form of a human hand for an outside surface is heated to a temperature between about 70° to about 95° C. and dipped into a first bath containing a PVC plastisol, or a PVC copolymer with maleic or acrylic esters and the like as a plastisol, maintained at a temperature between about 35° to about 45° C. The PVC plastisol preferably includes a polyvinyl chloride dispersion resin having an intrinsic viscosity between about 0.7 to about 1.5 (ASTM D-1243 Method A); a plasticizer, preferably phthalate or adipate mono or diesters having between 7 to 10 carbon atom chains and blends thereof, a stabilizer component and a pigment. The plastisol may also include viscosity modifiers, antifoam agents and the like. The mold residence time in the first bath, the solids content of the bath and the temperature all effect the thickness of the film formed. Preferably, the residence time is sufficient to allow the plastisol to form a film between about 0.03 mm to about 0.14 mm depending upon the desired film thickness and intended application for the glove. The resin to plasticizer ratio is preferably between about 0.8:1 to about 1.2:1.

The mold having the plastisol film on its surface is then removed from the first bath and placed in an oven to gel and fuse the plastisol film. The oven conditions and residence time preferably are sufficient to raise the temperature of the film to between about 160° C. to about 195° C.

The gelation and fusion process takes the plastisol compound from the liquid state to a substantially homogeneous solid film. The gelation and fusing process involves solvation of the resin by the plasticizer at an elevated temperature. Plasticizers are relatively poor solvents at ambient temperature, but at elevated temperatures, they dissolve or fuse the resin with subsequent development of physical properties, elongation, tensile strength, and resilience. In the present invention, the plastisol in the first bath must be maintained at a temperature sufficient to wet and suspend the PVC resin particles, but below a temperature where gelation and fusion occurs. Once the mold with the liquid plastisol film on its surface is removed from the bath, it is drained, then oven heated to induce gelation and fusion. The exact time and temperature for these steps will depend upon the specific resin, plasticizer, resin/plasticizer ratio, desired film thickness, and desired through-put rate for the glove manufacture.

Following the gelation and fusion, the mold having the fused PVC film on its surface is cooled, which serves to strengthen the film and cool the film to between about 75° C. to about 90° C. The mold having the first film on its surface is the dipped in a second bath including an aqueous suspension of a polyester polyurethane and a texturizing agent to form a second film of the polyurethane and the texturizing agent over the first film. The second bath preferably contains between about 5 to about 30 percent solids and preferably includes a polyester polyurethane to serve as a binder, a slip agent to allow surface mobility, a suspending agent and the texturizing agent. A preferred polyester polyurethane is Solucote 1051 I-35 at about 13 to about 17 percent by weight. Suitable slip agents are oxidized high density polyethylenes having a weight averaged molecular weight of about 10,960 daltons with an acceptable range between [about 2500] 8000 to [about 4000] 12000 daltons and a number averaged molecular weight of about 2819 daltons with an accetable range between [about 7,500] 1500 to [about 12,500] 4000 daltons. The preferred oxidized polyethylene is an aqueous emulsion and has a mean particle size between about 25 to about 50 nanometers ($10^{-9}$ meters). The slip agent is present in the second bath as an aqueous emulsion at between about 7 to about 20 percent. The slip agent serves to render the glove surface able to be hot stripped from the surface of the mold. The texturizing agent preferably is a finely divided material having a particle size distribution between about 1 and about 75 microns preferably between about 1 and about 50 microns. The finely divided material may be calcium carbonate diatomaceous earth, synthetic aluminosilicates, glass beads, silica, synthetic silicates and the like. The texturizing agent is present in the second bath between about 0.5 to about 2.0% (w/w). Preferably, the texturizing agent is calcium carbonate having a particle size distribution between about 1 to about 50 microns and present in about one percent (w/w) in the second bath. The second bath preferably also includes dispersing agents, surface active agents and antifoam agents. The mold having the first and second layers on its surface is then removed from the second bath and heated in an oven, drying the second film, adhering the second film to the first film and forming a two layer unitary structure on the mold surface. The unitary structure is maintained at a temperature between about 70° C. to about 90° C. and a cuff roll is formed on the unitary structure. The structure is then stripped and everted from the mold surface forming a glove having a patient contacting layer on an outside surface and a user contacting layer on an inside surface.

The finished gloves preferably are counted and packaged in shelf cartons.

Example 1

A clean mold having the form of a hand as an outside surface is heated to a temperature between about 70° C. to about 95° C. and dipped into a PVC plastisol bath maintained at about 35° C. to about 45° C. forming PVC plastisol film on its surface. The mold having the film on its surface is removed from the first bath, allowed to drain, then heated in an oven to raise the temperature of the film on the surface to between about 160° C. to about 195° C. forming a gelled and fused film with an average thickness about 0.08 mm. The film is cooled to between about 75° C. to about 90° C. and dipped in a second bath maintained at a temperature between about 35° C. and about 45° C. containing an aqueous emulsion including polyurethane, slip agent and texturizing agent to form a second film layer over the first layer. The mold having the first and second films is removed from the second bath and allowed to drain, then heated to about 70° C. to about 90° C. to dry and adhere the second layer to the first layer forming a unitary structure. A cuff is then formed on the unitary structure and the glove is stripped and everted forming a glove.

Composition of Baths for Example 1

| | Parts per 100 (weight/weight) |
|---|---|
| Materials-Bath 1 | |
| Geon 121X10 | 8.2 |
| NV2 Formolon | 42.3 |
| Jayflex DINP | 43.4 |
| Jayflex 215 | 1.9 |
| Drapex 4.4 | 1.5 |
| Interstab LT-4468 | 2.0 |
| Deplastol | 0.4 |
| Pigment | 0.3 |

-continued

Composition of Baths for Example 1

| | Parts per 100 (weight/weight) |
|---|---|
| Materials-Bath 2 | |
| Solucote 1051I-3-35 | 15.0 |
| Polyemulsion OA3N30 | 8.0 |
| Cabosperse A3875 | 6.0 |
| Duramite | 1.0 |
| Keltrol RD | 0.1 |
| Bubble Breaker 625 | 0.1 |
| Antarox LF330 | 0.5 |
| Water | Q.S. 100 |

Example 2

A clean mold having the form of a hand for an outside surface is heated to a temperature between about 70° C. to about 95° and dipped into a PVC plastisol bath maintained at a temperature between about 35° C. to about 45° C. to form a PVC plastisol film on its surface. The mold having the film on its surface is removed from the first bath, allowed to drain, then heated in an oven to raise the temperature of the film on the surface to between abut 160° C. to about 195° C. forming a gelled and fused film with an average thickness of about 0.08 mm. The film is cooled to between about 75° C. to about 90° C. and the mold having the film on its surface is dipped into a second bath maintained at between about 35° C. to about 45° C. containing an aqueous emulsion including polyurethane, slip agent and texturing agent to form a second layer over the first layer. The mold having the first and second layers on its surface is heated to between about 70° C. to about 90° C. to dry and adhere the second layer to the first layer forming a unitary structure. A cuff is then formed on the unitary structure and the structure is stripped and everted forming a glove.

Composition of Baths for Example 2

| | Parts per 100 (weight/weight) |
|---|---|
| Materials for Bath 1 | |
| Oxy 80HC | 46.3 |
| Jayflex 215 | 1.3 |
| Jayflex 77 | 48.0 |
| Drapex 4.4 | 1.7 |
| Interstab CZ7-717 | 1.7 |
| Deplastol | 0.5 |
| pigment | 0.5 |
| Materials for Bath 2 | |
| Solucote 1051I-3-35 | 15.0 |
| Polyemulsion OAN30 | 8.0 |
| Cabosperse A3875 | 3.0 |
| Atomite | 1.0 |
| Keltrol RD | 0.1 |
| Anatarox LF-330 | 0.5 |
| water | Q.S. 100 |

Example 3

A clean mold having the form of a hand as an outside surface is heated to a temperature between about 70° C. to about 95° C. and dipped into a PVC copolymer plastisol bath maintained at about 35° C. to about 45° C. to form a plastisol film. The mold having the film on its surface is removed from the first bath, allowed to drain, then heated in an oven to raise the temperature of the film to between about 160° C.

to about 195° C. forming a gelled and fused film with an average thickness about 0.08 mm. The film is cooled between about 75° C. and about 90° C. and dipped in a second bath maintained at about 35° C. to about 45° C. containing an aqueous emulsion including polyurethane, slip agent and texturizing agent to form a second layer over the first layer. The mold having the first and second films on the surface is removed from the bath and allowed to drain, then heated to about 70° C. to about 95° C. to dry and adhere the second to the first layer forming a unitary structure. A cuff is then formed on the unitary structure and the structure is stripped and everted forming a glove.

Composition of Baths for Example 3

| | Parts per 100 (weight/weight) |
|---|---|
| Materials for Bath 1 | |
| NV2 Formalon | 36.0 |
| Pliovic MC-85 copolymer | 12.0 |
| Kodaflex DOTP | 44.0 |
| Kodaflex DOA | 4.3 |
| Interstab LT-4468 | 1.5 |
| Jayflex 215 | 1.5 |
| pigment | 0.7 |
| Materials for Bath 2 | |
| Impranil DLN | 10.0 |
| Polyethylene OA3 | 15.9 |
| BYK-345 | 0.4 |
| Cabosperse A3875 | 6.0 |
| Zeothix | 1.0 |
| Kelzan | 0.1 |
| Bubble Breaker 625 | 0.2 |
| water | Q.S. 100 |

A preferred embodiment of the present invention is a glove having physical properties as given below in Table II, but the present invention may form films between about 0.035 mm to about 0.150 mm for particular applications.

TABLE II

| | Mean Thickness (mm) | Strength |
|---|---|---|
| Cuff | 0.06 | Modulus at 200% between about 500 to about 1200 psi; |
| Palm | 0.11 | |
| Finger | 0.07 | Tensile Strength minimum psi above about 1700 psi; and |
| | | Ultimate Elongation minimum % above about 350. |

Figure 2A:
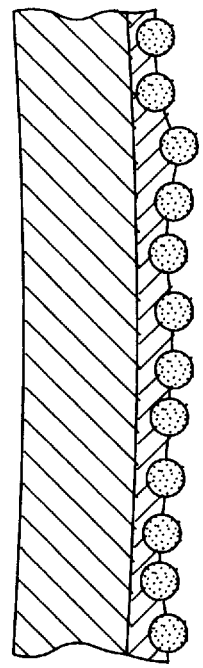
FIGS. 2a and 2b show a schematic cross sectional drawing of a glove surface from the prior art (2a) and a photomicrograph (2b) of a cross section and the surface of a glove of the present invention.
Figure 2B:
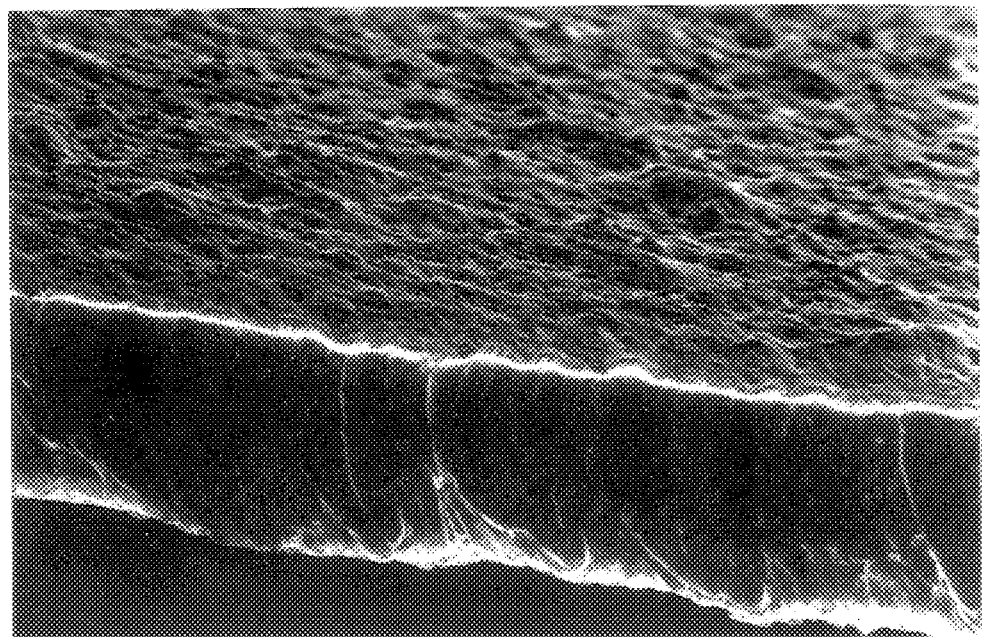

Referring to FIGS. 2a and 2b, a schematic drawing from the prior art taught by Stockum shows a surface of a glove having particulate material with a portion of the surface protruding through the surface of the adherent layer (FIG. 2a) and a photomicrograph of the surface of the present invention (FIG. 2b) for comparison shows the surface of the user contacting layer having the particulate material imbedded in and substantially covered by the polyester polyurethane.

The gloves of the present invention provide strength and tactile sensitivity similar to the well accepted powdered PVC gloves such as Tru-Touch™ while providing the added benefit of powder-free donnability.

What is claimed is:

1. A flexible article comprising:

a first layer comprising plasticized polyvinyl chloride resin; and a second layer adhered to said first layer comprising a polyester polyurethane, a slip agent comprising oxidized high density polyethylene having a weight average molecular weight between 8000 to 12000 daltons and a number average molecular weight between 1500 to 4000 daltons and a mean particle size between about 25 to about 50 nanometers, and a texturizing agent comprising a material having a particle size distribution between about 1 and about 75 microns selected from the group consisting of diatomaceous earth, silica, glass beads and calcium carbonate.

2. The flexible article of claim 1 wherein said first layer is a fused polyvinyl chloride gel plasticized with a plasticizer selected from the group consisting of adipate and phthalate esters.

3. The flexible article of claim 1 wherein said oxidized polyethylene has a weight averaged molecular weight of about 10,960 daltons and a number averaged molecular weight of about 2819 daltons.

4. A two layer glove for use in medical procedures comprising:

a first layer for contacting a patient formed as a film from a plasticized polyvinyl chloride resin; and a second layer for contacting a user adhered to said patient contacting layer formed as a film, said second layer comprising polyester polyurethane, and oxidized high density polyethylene slip agent having a weight average molecular weight between 8000 to 12000 daltons and a number average molecular weight between 1500 to 4000 daltons and a mean particle size between about 25 to about 50 nanometers, and a texturizing agent comprising a material having a particle size distribution between about 1 and about 75 microns selected from the group consisting of diatomaceous earth, silica, glass beads and calcium carbonate, thus providing a surface having texture so that said user contacting layer will slide on itself and a user's hand thereby rendering said glove donnable without the need for powder.

5. The glove of claim 4 wherein said patient contacting layer is formed from a fused polyvinyl chloride gel plasticized with a plasticizer selected from the group consisting of adipate and phthalate esters and blends thereof.

6. The glove of claim 4 wherein said glove has an average thickness between about 0.035 mm and about 0.150 mm.

7. The glove of claim 4 wherein said texturing agent has a particle size distribution between about 1 and about 50 microns and comprises calcium carbonate.

8. The glove of claim 4 wherein said oxidized polyethylene has a weight averaged molecular weight of about 10,960 daltons and a number averaged molecular weight of about 2819 daltons.

* * * * *